(12) United States Patent
Offenbeck et al.

(10) Patent No.: US 9,588,039 B2
(45) Date of Patent: Mar. 7, 2017

(54) OPTICAL MEASURING DEVICE

(71) Applicant: Hamilton Bonaduz AG, Bonaduz (CH)

(72) Inventors: Bernd Offenbeck, Regensburg (DE); Louis Willi, Bonaduz (CH)

(73) Assignee: Hamilton Bonaduz AG (CH)

( * ) Notice: Subject to any disclaimer, the term of this patent is extended or adjusted under 35 U.S.C. 154(b) by 0 days.

(21) Appl. No.: 14/653,889

(22) PCT Filed: Dec. 11, 2013

(86) PCT No.: PCT/EP2013/076167
§ 371 (c)(1),
(2) Date: Jun. 19, 2015

(87) PCT Pub. No.: WO2014/095506
PCT Pub. Date: Jun. 26, 2014

(65) Prior Publication Data
US 2015/0316469 A1    Nov. 5, 2015

(30) Foreign Application Priority Data
Dec. 21, 2012 (DE) .......................... 10 2012 113 024

(51) Int. Cl.
*H01J 40/14* (2006.01)
*G01N 21/27* (2006.01)
(Continued)

(52) U.S. Cl.
CPC ................ *G01N 21/27* (2013.01); *G01J 1/08* (2013.01); *G01J 1/46* (2013.01); *G01N 21/255* (2013.01);
(Continued)

(58) Field of Classification Search
CPC ................ G01N 21/27; G01N 21/255; G01N 2201/06113; G01N 2201/062; G01N 2201/0625
(Continued)

(56) References Cited

U.S. PATENT DOCUMENTS 4,660,977 A    4/1987  Wittner
4,807,630 A    2/1989  Malinouskas
(Continued)

FOREIGN PATENT DOCUMENTS

DE    693 31 629 T2    8/2002
DE    10 2005 012 625 A1    9/2006
(Continued)

OTHER PUBLICATIONS

English-language machine translation of DE 10 2010 063 933, Vonach, Jun. 28, 2012.
(Continued)

*Primary Examiner* — Kevin Pyo
(74) *Attorney, Agent, or Firm* — Jansson Munger McKinley & Kirby Ltd.

(57) ABSTRACT

A device for measuring a periodic signal is disclosed. The device includes a light source for generating an optical input signal directed at an object being measured from an electrical input signal generated by a driver device on the basis of a first clock pulse, an optical receiver for detecting and converting the signal received, a central control and measuring device is designed to generate the first clock pulse for the driver device and to receive and process the electrical measuring signal, and a voltage-supply apparatus for supplying the driver device. The central control and measuring device are preferably designed to generate a second clock pulse for the voltage-supply apparatus and to filter the electrical measuring signal on the basis of the first and/or
(Continued)

second clock pulse. The frequency of the second clock pulse is an even multiple of the frequency of the first clock pulse.

9 Claims, 6 Drawing Sheets

(51) Int. Cl.
*G01N 21/25* (2006.01)
*G01N 21/31* (2006.01)
*G01J 1/08* (2006.01)
*G01J 1/46* (2006.01)

(52) U.S. Cl.
CPC ... *G01N 21/3151* (2013.01); *G01N 2201/062* (2013.01); *G01N 2201/06113* (2013.01)

(58) Field of Classification Search
USPC ............ 250/205, 214 R; 315/291, 307, 360; 372/38.02, 38.07
See application file for complete search history.

(56) References Cited

U.S. PATENT DOCUMENTS

| | | | |
|---|---|---|---|
| 5,317,307 A | 5/1994 | Thomas, Jr. | |
| 5,323,008 A | 6/1994 | Studholme et al. | |
| 5,426,306 A | 6/1995 | Kolber et al. | |
| 6,548,967 B1 | 4/2003 | Dowling et al. | |
| 6,724,376 B2 * | 4/2004 | Sakura | H04B 10/508 327/109 |
| 6,989,701 B2 * | 1/2006 | Lin | H04B 10/524 327/109 |
| 7,005,646 B1 | 2/2006 | Jordanov et al. | |
| 7,009,440 B2 | 3/2006 | Nogawa et al. | |
| 7,095,002 B2 | 8/2006 | Kong et al. | |
| 7,564,046 B1 | 7/2009 | Hoang | |
| 7,598,683 B1 | 10/2009 | Jalbout et al. | |
| 7,638,950 B1 | 12/2009 | Jalbout et al. | |
| 7,723,899 B2 | 5/2010 | Blandino et al. | |
| 8,067,905 B2 | 11/2011 | Jalbout et al. | |
| 2003/0069486 A1 | 4/2003 | Sueppel et al. | |
| 2003/0174317 A1 | 9/2003 | Murdock et al. | |
| 2006/0231745 A1 | 10/2006 | Bodano et al. | |
| 2006/0289786 A1 | 12/2006 | Taylor et al. | |
| 2009/0240125 A1 | 9/2009 | Such et al. | |
| 2009/0261746 A1 | 10/2009 | Jalbout et al. | |
| 2010/0244929 A1 | 9/2010 | Jalbout et al. | |

FOREIGN PATENT DOCUMENTS

| | | |
|---|---|---|
| DE | 10 2006 041 013 A1 | 3/2007 |
| DE | 10 2010 063 933 A1 | 6/2012 |
| EP | 0 212 455 A2 | 3/1987 |
| EP | 0 241 268 A2 | 10/1987 |
| WO | 0178593 A1 | 10/2001 |
| WO | 2011120855 A1 | 10/2011 |

OTHER PUBLICATIONS

English-language machine translation of DE 10 2006 041 013, Weinmann G. Geraete Med., Mar. 15, 2007.

* cited by examiner

OPTICAL MEASURING DEVICE

RELATED APPLICATION

This application is a U.S. national stage entry of PCT/EP2013/076167 filed Dec. 11, 2013, which claims priority to German Patent Application No. 10 2012 113 024.8 filed Dec. 21, 2012, the contents of both applications being incorporated herein by reference in their entirety.

FIELD OF THE INVENTION

The present invention pertains to the field of process measurement technology and analysis and, more specifically, to the field of optical measuring devices for measuring periodic signals.

BACKGROUND OF THE INVENTION

In sensors of process measurement technology and analysis, optical measuring methods are being used more and more frequently. In these methods, the amplitude and/or phasing of an optical signal changes when it strikes a measurement object, and the changed signal is detected by an optical sensor. An example of the application of an optical measuring method of this type is the measurement of the oxygen content or oxygen saturation of a liquid or of a substance, wherein, for example, a dye is illuminated by a light signal of a previously determined wavelength, amplitude, and phasing, and the luminescent light reflected from the dye is analyzed. When the oxygen concentration in the dye changes, the fade time of the luminescence and thus the amplitude and phasing of the received optical signal also change. With appropriate calibration, the amplitude and phase of the received optical signal are therefore a measure of the oxygen concentration.

Measuring devices of this type must be suitable for use in many areas, simple in design, and as interference-proof as possible against external and internal influences and side effects. For example, they are used in areas at risk of explosion and therefore must consume the least possible amount of energy and thus be assembled from relatively uncomplicated or simple components. In addition, the economic constraints must also be taken into account by using reliable, mass-produced components that are commercially available at low cost.

For this purpose, the functionalities of different components are frequently bundled into microcontrollers; that is, in addition to a data processing microprocessor, other digital or analog components, peripheral functions, or interfaces are also integrated into a microchip. When additional analog or digital components such as a voltage-supply circuit or a driver circuit are used outside the microcontroller of an optical measuring device, direct interference with certain components may occur; or indirect interference may result from parasitic effects originating from power supply lines. Measurement signals can therefore be inaccurate or their evaluation negatively affected, and the result is that the function of the entire measuring device is impaired.

It is therefore the object of the present invention to provide an optical measuring device which largely avoids direct or indirect interference with electronic components, which can be built easily at low cost, and which makes reliable measurement possible.

This object is achieved by the invention described and claimed herein. Particularly advantageous forms and embodiments of the invention are also described and claimed.

SUMMARY OF THE INVENTION

According to the invention, a device for measuring a periodic signal comprises: a light source for generating an optical input signal directed at an object being measured from an electrical input signal generated by a driver device on the basis of a first clock pulse; an optical receiver for detecting and converting the signal received from the object being measured, the signal corresponding to the optical input signal altered in terms of phase and amplitude into an electrical measuring signal; a central control and measuring device which is designed to generate the first clock pulse for the driver device and to receive and to process the electrical measuring signal; and a voltage-supply apparatus for supplying the driver device, wherein the central control and measuring device is designed to generate a second clock pulse for the voltage-supply apparatus and to filter the electrical measuring signal on the basis of the first and/or second clock pulse; and wherein the frequency of the second clock pulse is an even multiple of the frequency of the first clock pulse. As a result of the synchronicity of the second clock pulse as an exact, even multiple of the first clock pulse and thus of the electrical measuring signal, interference which acts via the supply lines directly on the light source or interference which may occur as a result of parasitic effects, such as capacitances between the supply lines between the control and measurement unit and the voltage-supply apparatus or the driver device, are effectively avoided.

It is especially advantageous for the light source to be configured as an LED or laser. Light sources of this type are mass-produced and obtainable at low cost.

It is also advantageous for the voltage-supply apparatus to be configured as a charge pump. Charge pumps transport the electrical charge by means of electrical capacitors and by periodic changeover of switches, as a result of which it is possible to generate electrical output voltages on different levels. In a simple example, a charge pump is fed with direct voltage and generates as output a direct voltage which is twice as high and has the same polarity. For the periodic changeover, an oscillator is used for a charge pump of this type, or a periodic switching pulse must be supplied from the outside. In the case of the present invention, the periodic switching signal can be provided by a control and measuring unit, and a simple DC voltage-supply apparatus operating, e.g., at 2V, can be used as the DC power source. When the charge pump is being operated by the second clock pulse, the power lines to the driver device cause interference, which negatively affects the electrical measuring signal for the light source. As a result of the frequency of the second clock pulse appropriately selected according to the invention relative to the frequency of the first clock pulse, this interference is filtered out.

It is especially preferable for the central control and measuring device to comprise a lock-in amplifier. A lock-in amplifier is also called a phase-sensitive rectifier or carrier-frequency amplifier, which is able to measure a weak alternating electrical signal modulated by a reference signal of known frequency and phase. Thus the lock-in amplifier represents an extremely narrow-band band-pass filter and thereby improves the signal-to-noise ratio (SNR).

In the present invention, it is especially advantageous for the central control and measuring device to be configured as a microcontroller and for this microcontroller to comprise an analog or digital lock-in amplifier integrated appropriately into it.

It is also advantageous for the control and measurement unit to comprise a pulse width modulation (PWM) generator. This PWM generator may also be an integrated component of the microcontroller. In particular, it is possible in this way for the first clock pulse for actuating the driver device to be formed as a square wave signal by the PWM generator. For this purpose, there is no need for any calculations to be performed in the microprocessor of the microcontroller itself to generate the desired signals. The use of a PWM generator is therefore thrifty with respect to both resources and energy. The central control and measuring device can also advantageously comprise a CMOS switch or CMOS changeover switch to control the first and/or second clock pulse.

An analog or digital preamplifier is preferably connected between the optical receiver and the central control and measuring device. Because of the small amplitudes of the electrical measuring signal, the use of a preamp can be useful. As a result of the suitable selection of the frequencies of the first and second clock pulses, the device according to the invention also takes into account the possibility that interference signals can be introduced as a result of the high sensitivity of the preamp.

BRIEF DESCRIPTION OF THE DRAWINGS

The present invention is described below with reference to certain preferred embodiments illustrated in the following drawings.

DETAILED DESCRIPTIONS OF PREFERRED EMBODIMENTS

Figure 1:
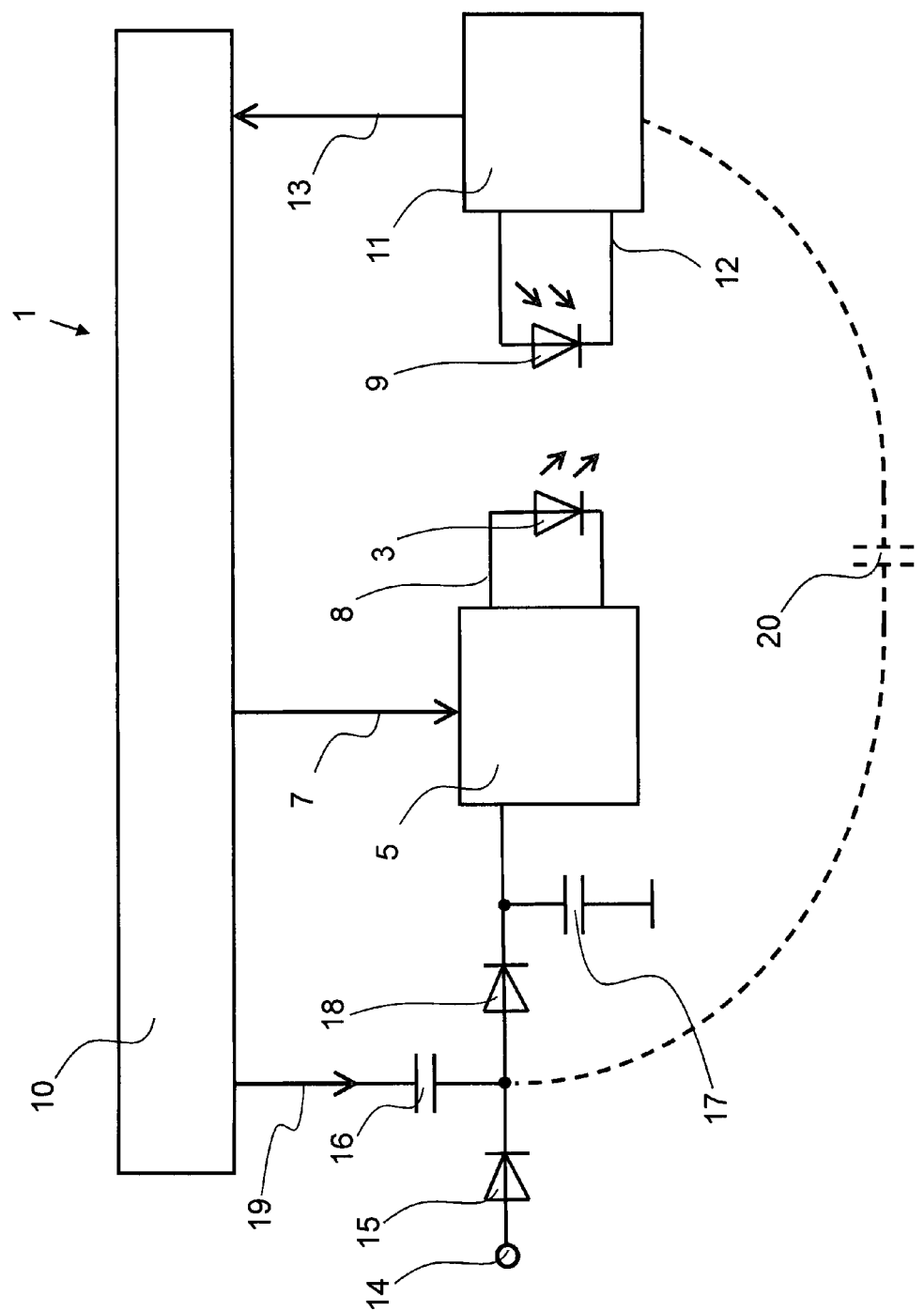
FIG. 1 is a schematic circuit diagram of a preferred embodiment of an optical measuring device in accordance with this invention.

FIG. 1 shows a schematic circuit diagram of a preferred embodiment of the device according to the invention for measuring a periodic signal. Device 1 comprises a light source 3 for generating an optical input signal, directed at an object being measured (not shown), from an electrical input signal 8 generated by a driver device 5 on the basis of a first clock pulse 7. First clock pulse 7 is generated by a central control and measuring device 10, which is described in greater detail below.

An optical receiver 9 acquires the signal received from the object being measured, wherein said received signal corresponds to the optical input signal which has been altered in terms of its phase and amplitude, and converts it into an electrical measuring signal 12. Electrical measuring signal 12 is amplified in a preamplifier 11 and sent as an amplified electrical measuring signal 13 to central control and measuring device 10.

Central control and measuring device 10, in the preferred embodiment, is configured as a microcontroller and has the functionality of generating first clock pulse 7 and also of receiving and processing and/or evaluating amplified electrical measuring signal 13.

Device 1 according to the invention also includes a voltage-supply apparatus for supplying driver device 5. In the preferred embodiment, the voltage-supply apparatus is configured as a charge pump and comprises: a DC power source 14; two series-connected diodes 15, 18; a pump capacitor 16; and an output capacitor 17. Pump capacitor 16 is supplied with second clock pulse 19 from central control and measuring device 10. Present at DC power source 14 is, e.g., a DC voltage of 2 volts. It should be pointed out here that the invention also pertains to embodiments with other power supplies working with different clock pulses or signals, e.g., cascaded charge pumps with voltage multiplication.

The function of the charge pump of the preferred embodiment is explained briefly as follows: In the first state, the second clock pulse 19 is present at pump capacitor 16 and charges pump capacitor 16 via diode 15 to the input voltage of DC power source 14, which, e.g., is 2 volts. Then central control and measuring device 10 turns off second clock pulse 19. As a result, the input voltage and the voltage of pump capacitor 16 are in series, as a result of which diode 15 is back-biased, i.e., blocked, and diode 18 is conducting. Output capacitor 17 is therefore charged to approximately twice the input voltage of DC power source 14. This voltage is now applied at driver device 5. After that, the cycle repeats in correspondence with the periodicity of second clock pulse 19. Twice the voltage of DC power source 14 is therefore applied at driver device 5 at the timing of second clock pulse 19.

Using the timing of first clock pulse 7, driver device 5 actuates light source 3 by means of electrical input signal 8. Thus light source 3, with the timing based on electrical input signal 8, generates an optical input signal, which is directed at an object being measured (not shown). Optical receiver 9 receives the optical input signal, the amplitude and phase of which have been changed by the object being measured, and converts it into an electrical measuring signal 12. Electrical measuring signal 12 is amplified as appropriate in preamp 11 and sent to a measurement input of central control and measuring device 10 as amplified electrical measuring signal 13.

As a result of the voltage-supply apparatus of driver device 5, interference can occur especially as a result of the actuation by means of second clock pulse 19; this interference can influence driver device 5 and thus light source 3 directly by way of the supply lines, or the interference signals arising from parasitic effects can exert an indirect influence on the components of the receiving and measurement area, i.e., optical receiver 9 and preamp 12, and thus influence electrical measuring signals 12 and/or 13. A feedback effect by the alternating load of the charge pump as a result of DC voltage-supply apparatus 14 is also possible. Another possible influence can be attributed to interference with the voltage-supply apparatus of optical receiver 9, which is not contained in the embodiment shown here. In the schematic diagram of FIG. 1, the stray capacitance 20 is representative of all of the negative interference effects which can falsify the measurement of the optical signal.

These interference signals, which may arise on the basis of second clock pulse 19, which controls the voltage-supply apparatus, which, in the preferred embodiment is configured as a charge pump, are suppressed according to the invention in suitable fashion in that the frequency of second clock pulse 19 is an even multiple of the frequency of first clock pulse 7. It must be kept in mind here that central control and measuring device 10 is advantageously configured as a microcontroller, which, in addition to the microprocessor, also comprises appropriate peripheral functionalities on a chip. In particular, the microcontroller comprises appropriate elements which can synchronously generate first and second clock pulses 7, 19 and which can also process amplified electrical measuring signal 13. This means that the generation and/or evaluation of the corresponding signals can be coordinated with each other very accurately in time, which results in highly synchronous phasing.

To explain the device according to the invention in greater detail, measurement signal curves and corresponding auxiliary signals for various signal forms and frequencies of first clock pulse 7 and thus of the electrical measuring signal are shown in FIGS. 2a-2e. In central control and measuring device 10, a simple lock-in measurement method serves as the starting point. For a certain period of time, light source 3 is turned on by driver device 5 on the basis of first clock pulse 7. During this time, electrical measuring signal 13, detected by optical receiver 9 and appropriately preamplified, is processed in the lock-in amplifier of central control and measuring device 10. A process of integration is carried out; that is, an average value is formed over all of the measurement points. Then in correspondence with the signal curve of first clock pulse 7, light source 3 is turned off for the same period of time, and amplified electrical measuring signal 13 is also integrated in the lock-in amplifier of central control and measuring device 10. The results obtained for the two half-periods are subtracted from each other, from which the amplitude of the measurement signal is obtained.

Steady components, e.g., components caused by daylight, are very effectively suppressed by this type of measurement signal processing, because they are present equally in the measurement during the turned-on phase (of light source 3), and cancel each other out of the measurement during the turned-off phase (of light source 3). When this method is repeated frequently, as is usual in the case of a lock-in measurement, i.e., over a large number of measurement cycles, frequencies even far outside the measurement range are also very effectively suppressed.

Each of FIGS. 2a-2e shows a plurality of signal curves, i.e., their amplitudes, over time. The time comprises the duration of a period, that is, a half-period in which light source 3 sends an optical measurement signal and a half-period in which no optical measurement signal is sent by light source 3. The entire period is divided into sixteen subsections, wherein the interference-free measurement signal is indicated by a diamond at each of the sixteen time points. The interference-free measurement signal has an amplitude of 0.8 at time points 1 to 8 and goes down to a value of 0 at time points 9 to 16. The integration of the measurement signal is represented by a signal curve which has the value of +1 at time points 1 to 8 (the integration signal is indicated by squares) and a value of −1 at time points 9 to 16. The integration of the interference-free measurement signal means multiplying the signal values by +1 in first half-period (time points 1 to 8) and multiplying by −1 in the second half-period (time points 9 to 16). Then the average value of the first half-period and the average value of the second half-period are determined, and the average value of the second half-period is subtracted from the average value of the first half-period, resulting in the average signal amplitude over the entire range.

Figure 2A:
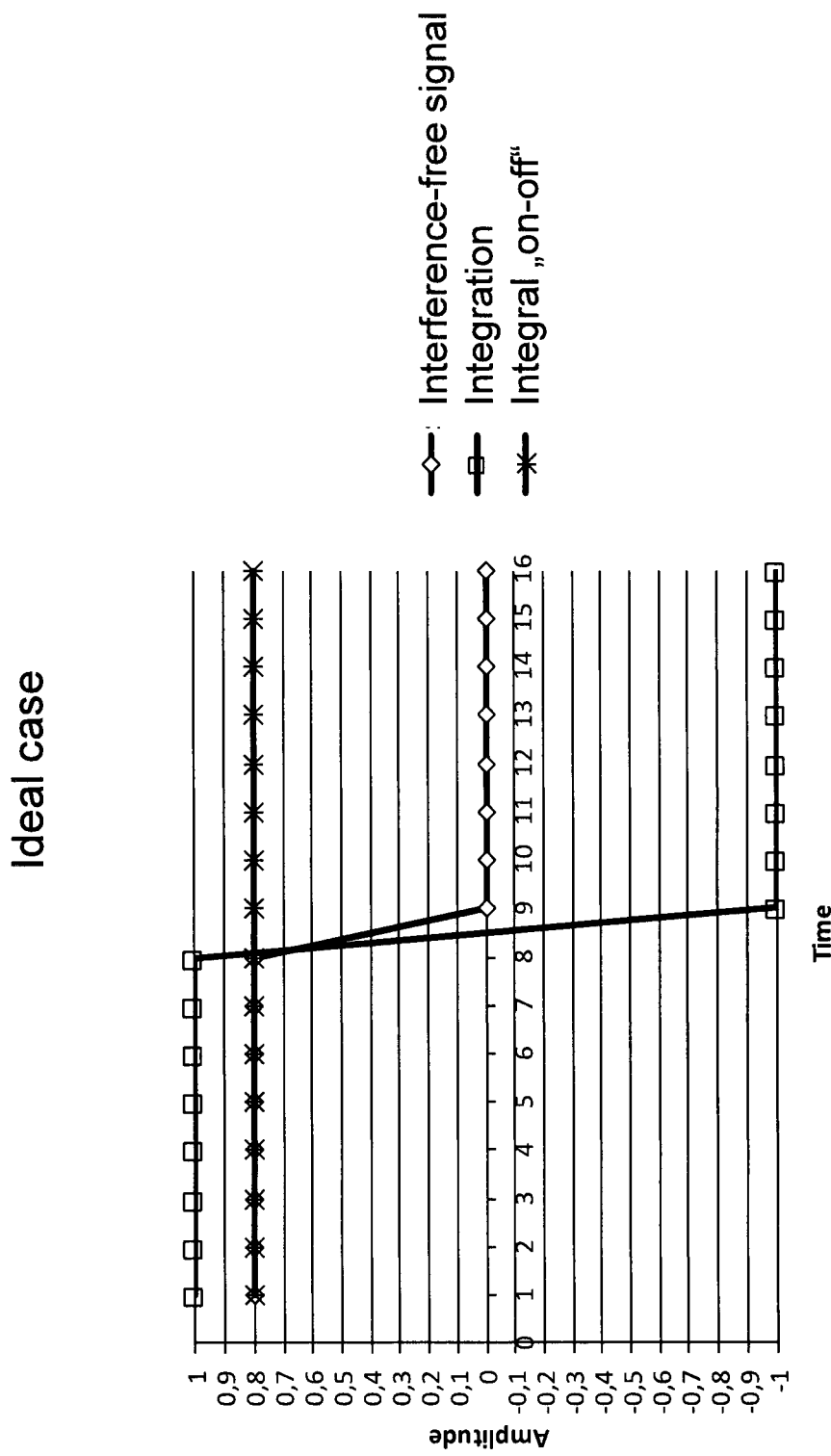
FIGS. 2a-2e are illustrative measurement signal curves for various embodiments and frequencies of the first and second clock pulses.

FIG. 2a shows the interference-free measurement signal with a value of 0.8 in the first half-period and with a value of 0 in the second half-period. After multiplication by +1 in the first half-period and −1 in the second half-period, we obtain an average value for the first half-period of 0.8 and an average value for the second half-period of 0. Overall, what is obtained for the entire time (time points 1 to 16) is a value of 0.8, which is exactly the expected original amplitude of the measurement signal.

Figure 2B:
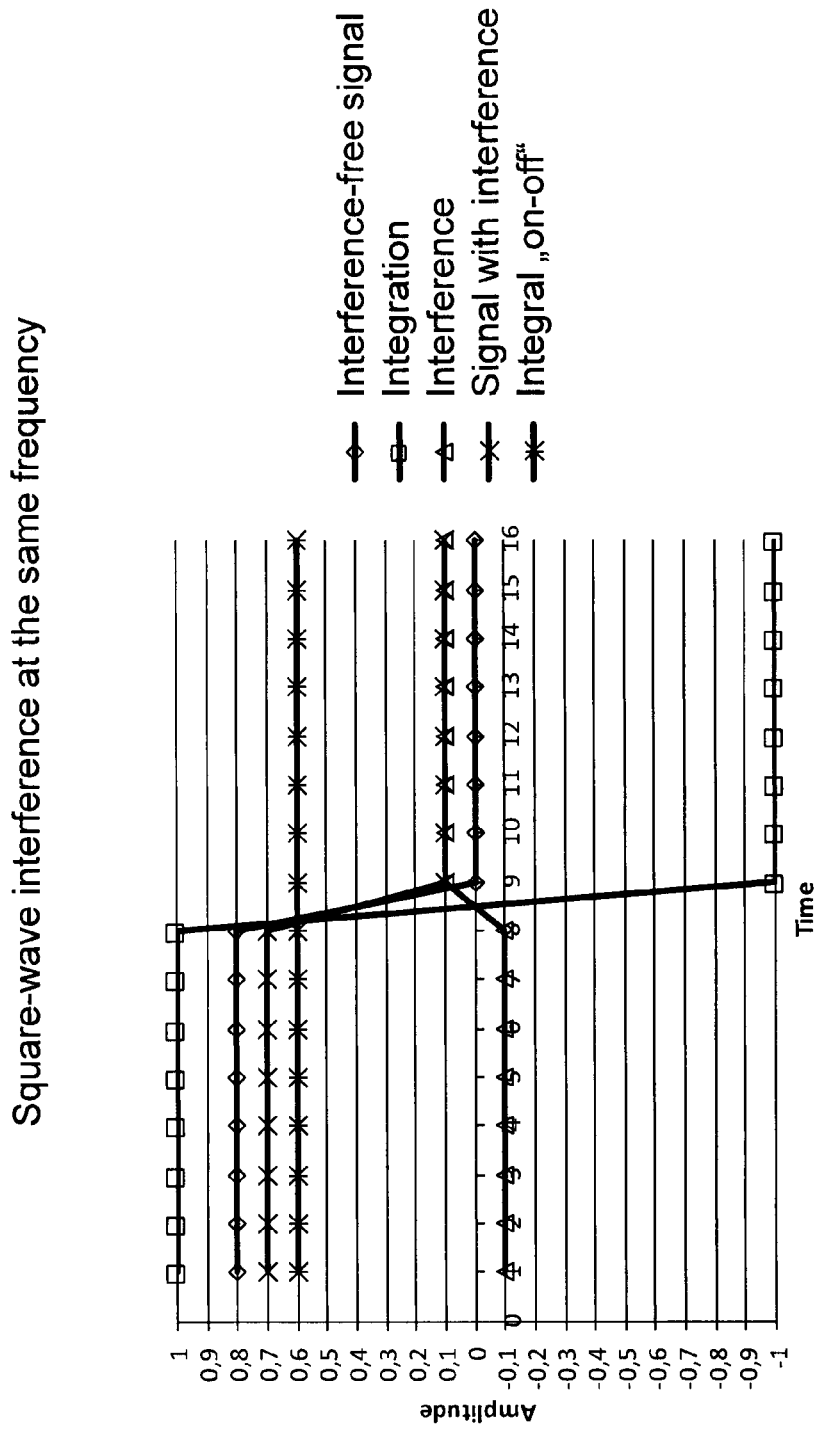

FIG. 2b now shows the influence which square-wave interference of the same frequency as that of first clock pulse 7 exerts on the measurement signal. The interference-free measurement signal, as in FIG. 2a, is 0.8 in the first half-period and 0 in the second half-period. A square-wave interference is also shown, which has a value of −0.1 in the first half-period and a value of +0.1 in the second half-period. The two signals, i.e., the interference-free measurement signal and the interference signal, are now added together and plotted as another curve (indicated by a simple cross), wherein a value of 0.7 is obtained for the first half-period and a value of 0.1 for the second half-period, namely, after the integration as described above. For the first half-period, integration means multiplying the signal with interference by a value of +1 and in the second half-period multiplying it by the value −1. This results in an integrated measurement signal with a value of 0.6 in both half-periods, which is obtained by combining the average value 0.7 in the first half-period and the average value −0.1 in the second half-period, and thus, by addition, a value of +0.6. For the exemplary embodiment shown in FIG. 1, this signal curve of FIG. 2b means that the charge pump is running on exactly the same second clock pulse 19 as the measurement controlled by first clock pulse 7. The interference thus leads to a negative influence on the measurement of the amplitude.

Figure 2C:
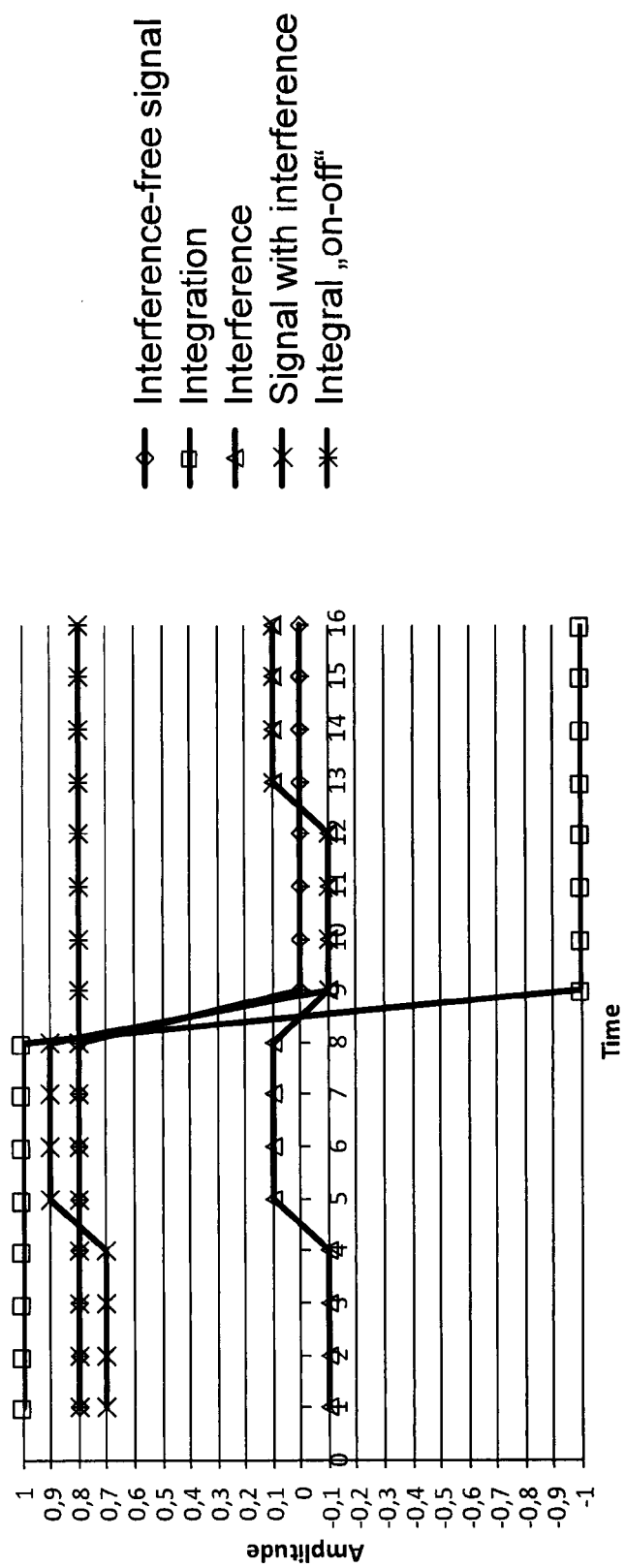

FIG. 2c now shows a square-wave interference similar to that of FIG. 2b over the entire course of the signal, except that now the square-wave interference is at twice the frequency; that is, the second clock pulse 19, which causes the interference, has exactly twice the frequency of first clock pulse 7. The square-wave interference at twice the frequency, indicated by triangles, therefore has four values of −0.1 and four values of +0.1 in the first half-period and analogous, corresponding values in the second half-period. After integration and average value formation, an average value of 0.8 is obtained for the first half-period, from which an average value of 0 is subtracted for the second half-period, resulting overall in an average value of 0.8 for the entire period, i.e., exactly the interference-free measurement signal. FIG. 2c therefore shows that, at exactly twice the frequency of second clock pulse 19 relative to first clock pulse 7, interference can be completely suppressed. In other words, the measurement signal based on first clock pulse 7 and the control signal for the charge pump (second clock pulse 19) at twice the frequency are therefore perfectly synchronous in time, and therefore the best possible suppression of the interference is achieved.

Figure 2D:
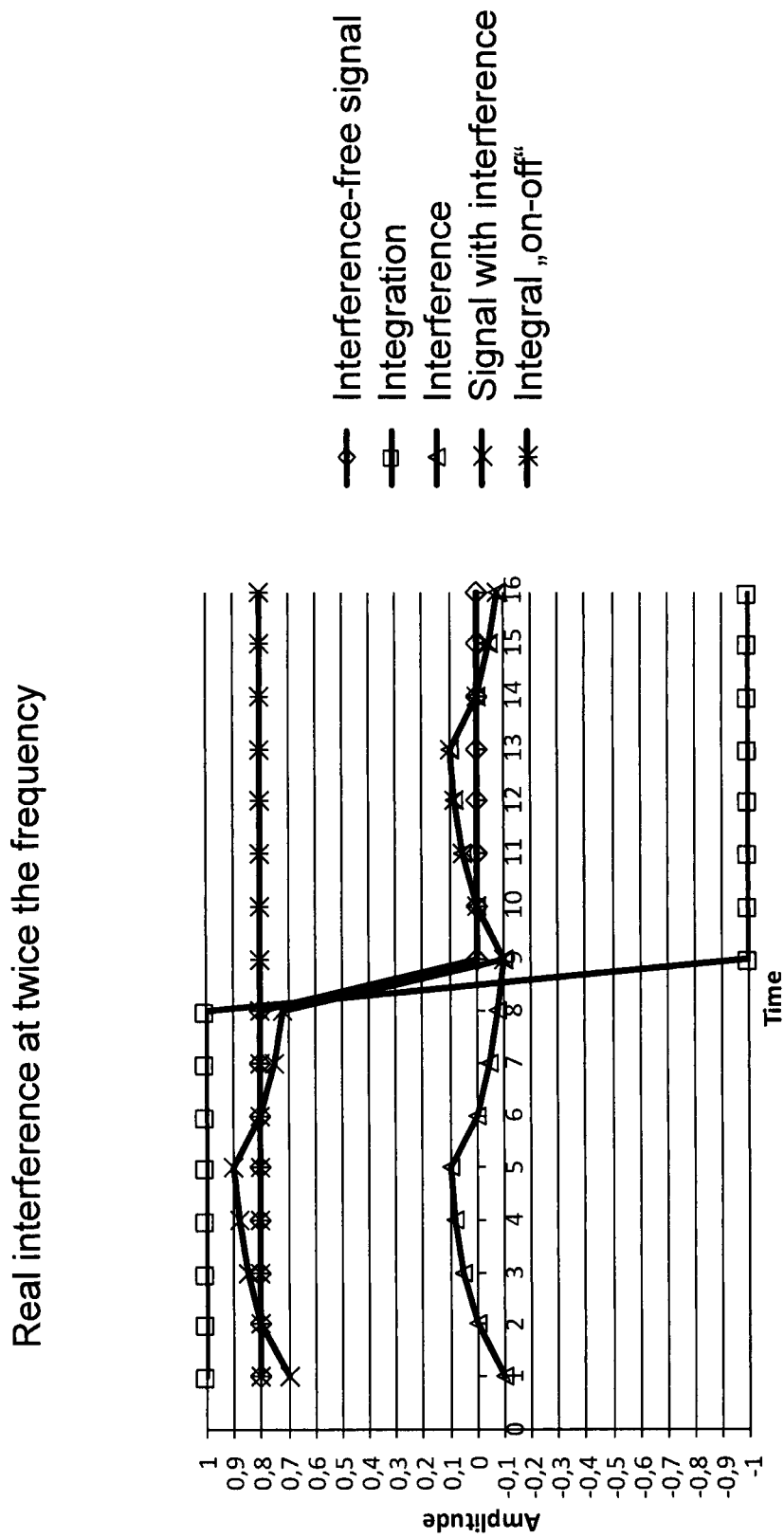

In reality, however, an interference signal is not a square wave; on the contrary, it will have a course which is distorted in some way or other. FIG. 2d shows the scenario with this type of real interference at twice the frequency of the first clock pulse. In the diagram of FIG. 2d, it is assumed that the interference signal is scattered at twice the frequency of the measurement signal but consists of symmetric exponential transients. This can be the case when, for example, the decoupling capacitors are too small, as a result of which the charge pump has a feedback effect on the voltage-supply apparatus of optical receiver 9, or when capacitive coupling occurs via stray capacitance 20. It can be seen that, with this type of interference as well, which can very easily occur in reality, the amplitude measurement continues to yield the correct measurement signal, because the interference signal is averaged out within each time section, i.e., over the two half-periods.

Figure 2E:
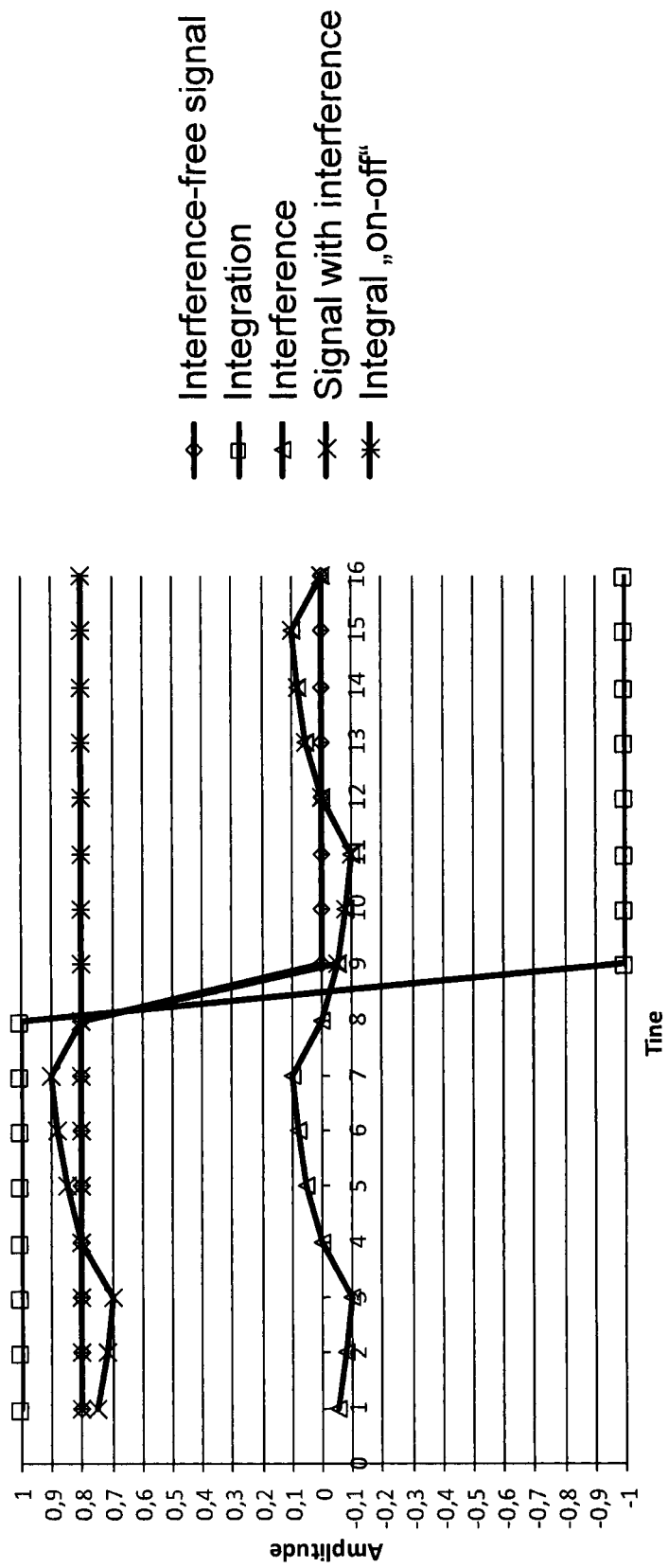

In addition to the real interference signal of FIG. 2d, FIG. 2e also shows a phase shift built into the interference signal, namely, a shift by two time points. In this case, too, the interference within one period of a measurement section is canceled completely out. It has therefore been shown that the device according to the invention is also effective in suppressing real, phase-shifted interference at twice the frequency of the first clock pulse.

The person skilled in the art will understand on the basis of the description given above that the averaging-out of interference signals can be used not only for the frequency which is twice that of second clock pulse 19 relative to first clock pulse 7 of the preferred embodiment of the present invention, but also for the n-fold frequency, because the corresponding components will always cancel each other out of the two half-periods.

In addition, it is obvious that the device according to the invention applies not only to the change in amplitude shown in FIGS. 2a-2e but also to interference which contains different phase positions of the optical signal.

In keeping with the object of the invention, an optical measuring device has been provided in which the direct or indirect interference with electronic components is almost completely avoided, which can be built easily and at low cost, and which makes reliable signal measurement possible.

The invention claimed is:

1. A device for measuring a periodic signal comprising:
   a light source for generating an optical input signal directed at an object being measured from an electrical input signal generated by a driver device on the basis of a first clock pulse;
   an optical receiver for detecting and converting the signal received from the object being measured, the received signal corresponding to the optical input signal altered in terms of phase and amplitude, into an electrical measuring signal;
   a central control and measuring device designed to generate the first clock pulse for the driver device and to receive and to process the electrical measuring signal; and
   a voltage supply apparatus for supplying the driver device, wherein the central control and measuring device is designed to generate a second clock pulse for the voltage supply apparatus and to filter the electrical measuring signal on the basis of the first and/or second clock pulse, wherein the frequency of the second clock pulse is an even multiple of the frequency of the first clock pulse.

2. The device of claim 1 wherein the light source is configured as an LED or laser.

3. The device of claim 1 wherein the voltage supply apparatus is configured as a charge pump.

4. The device of claim 1 wherein the central control and measuring device comprises a lock-in amplifier.

5. The device of claim 1 wherein the central control and measuring device is configured as a microcontroller.

6. The device of claim 1 wherein the central control and measuring device comprises a pulse width modulation (PWM) generator.

7. The device of claim 1 wherein the first clock pulse is formed as a square wave signal.

8. The device of claim 1 wherein the central control and measuring device comprises a CMOS switch or CMOS changeover switch.

9. The device of claim 1 wherein a preamplifier is connected between the optical receiver and the central control and measuring device.

* * * * *